United States Patent
Bassindale et al.

(10) Patent No.: US 11,007,548 B2
(45) Date of Patent: May 18, 2021

(54) ATOMISER SYSTEM FOR DISPENSING A FRAGRANCE

(71) Applicant: RECKITT BENCKISER (BRANDS) LIMITED, Berkshire (GB)

(72) Inventors: Philip Bassindale, Yorkshire (GB); Arron Bird, Greater Manchester (GB); James Brunt, Yorkshire (GB); James Crees, Yorkshire (GB); Avijit Das, Yorkshire (GB)

(73) Assignee: RECKITT BENCKISER (BRANDS) LIMITED, Slough (GB)

( * ) Notice: Subject to any disclaimer, the term of this patent is extended or adjusted under 35 U.S.C. 154(b) by 13 days.

(21) Appl. No.: 16/308,059

(22) PCT Filed: Jun. 14, 2017

(86) PCT No.: PCT/GB2017/051723
§ 371 (c)(1),
(2) Date: Dec. 7, 2018

(87) PCT Pub. No.: WO2017/216548
PCT Pub. Date: Dec. 21, 2017

(65) Prior Publication Data
US 2019/0308215 A1 Oct. 10, 2019

(30) Foreign Application Priority Data
Jun. 17, 2016 (GB) .................................... 1610656

(51) Int. Cl.
| | | |
|---|---|---|
| *B05B 17/06* | (2006.01) | |
| *A61K 8/04* | (2006.01) | |
| *A61K 8/31* | (2006.01) | |
| *A61L 9/01* | (2006.01) | |
| *A61L 9/12* | (2006.01) | |
| *A61Q 13/00* | (2006.01) | |
| *B05B 17/00* | (2006.01) | |
| *A01M 1/20* | (2006.01) | |

(52) U.S. Cl.
CPC ......... *B05B 17/0684* (2013.01); *A01M 1/205* (2013.01); *A61K 8/046* (2013.01); *A61K 8/31* (2013.01); *A61L 9/01* (2013.01); *A61L 9/127* (2013.01); *A61Q 13/00* (2013.01); *B05B 17/0646* (2013.01); *A61K 2800/87* (2013.01); *A61L 2209/132* (2013.01)

(58) Field of Classification Search
CPC ............ B05B 17/0684; B05B 17/0646; A01M 1/205; A61K 8/046; A61K 8/31; A61K 2800/87; A61L 9/01; A61L 9/127; A61L 2209/132; A61Q 13/00
USPC .......................... 239/4, 44, 102.1, 202.2, 145
See application file for complete search history.

(56) References Cited

U.S. PATENT DOCUMENTS

| | | | |
|---|---|---|---|
| 4,304,688 | A | 12/1981 | Mori |
| 6,341,732 | B1 | 1/2002 | Martin et al. |
| 6,386,462 | B1* | 5/2002 | Martens, III ........ B05B 17/0646 239/102.2 |
| 6,446,880 | B1 | 9/2002 | Schram et al. |
| 2001/0042794 | A1 | 11/2001 | Tomkins et al. |
| 2006/0011733 | A1* | 1/2006 | Varanasi ............... A01M 1/205 239/102.2 |
| 2006/0011737 | A1 | 1/2006 | Amenos et al. |
| 2007/0231290 | A1 | 10/2007 | Robinson et al. |
| 2008/0011874 | A1* | 1/2008 | Munagavalasa .... B05B 17/0684 239/102.2 |
| 2008/0041972 | A1 | 2/2008 | Chen et al. |
| 2009/0224064 | A1* | 9/2009 | Brodbeck ................. A61L 9/03 239/6 |
| 2011/0132992 | A1 | 6/2011 | Hoppe et al. |
| 2011/0318276 | A1 | 12/2011 | Nguyen et al. |
| 2015/0306623 | A1* | 10/2015 | Kawano ................ A01M 1/205 239/102.2 |
| 2017/0165391 | A1* | 6/2017 | Banco ..................... A61L 9/013 |

FOREIGN PATENT DOCUMENTS

| | | |
|---|---|---|
| EP | 1 474 245 A1 | 11/2004 |
| JP | 3342095 B2 | 11/2002 |
| JP | 2014 008494 A | 1/2014 |
| JP | 2014 046302 A | 3/2014 |
| WO | 2003 068413 A1 | 8/2003 |
| WO | 2009 142955 A1 | 11/2009 |
| WO | 2010 134164 A1 | 11/2010 |
| WO | 2016 049398 A1 | 3/2016 |

OTHER PUBLICATIONS

ExxonMobil Chemical, Product Safety Summary (ISOPAR M Fluid), Mar. 2016, pp. 1-3. (Year: 2016).*
Parchem Fire & Specialty Chemicals, Safety Data Sheet (ISOPAR M), Dec. 2, 2015, pp. 1-10. (Year: 2015).*
International Search Report and Written Opinion issued by the European Patent Office dated Aug. 28, 2017.
Combined Search and Examination Report issued in corresponding application GB 1610656.9 dated Nov. 24, 2016.
Chemicals Idemitsu Kosan Co. Ltd: "Idemitsu Kosan Co.,Ltd",, Mar. 8, 2016 (Mar. 8, 2016), XP055727047, Retrieved from the Internet: URL:http://www.idemitsu-chemicals.de/files/datasheets/broschures/PerformanceChemicals/IPSolvent.pdf.
EP Office Action Communication in corresponding application EP 17732160.1 dated Jan. 29, 2021.

* cited by examiner

*Primary Examiner* — Steven J Ganey
(74) *Attorney, Agent, or Firm* — Norris McLaughlin PA

(57) ABSTRACT

An atomiser device for dispensing a fragrance composition into the air. The device comprising an ultrasonic atomiser and a refill comprising a fragrance composition. The invention also includes a method of fragrancing the air utilising the atomiser device. A refill of the fragrance composition suitable for use in the atomiser device.

20 Claims, No Drawings

ATOMISER SYSTEM FOR DISPENSING A FRAGRANCE

This is an application filed under 35 USC 371 based on PCT/GB2017/051723, filed 14.Jun.2017, which in turn is based on GB 1610656.9 filed 17.Jun.2016. The present application claims the full priority benefit of these prior applications and herein incorporates by reference the full disclosures of these prior applications.

BACKGROUND TO THE INVENTION

Ultrasonic atomisers have long been used to vapourise liquid fragrance compositions to freshen the air. They offer advantages over alternative methods (heated liquid electricals/candles for example) in that they do not require heating to operate. Which means they are safer, no naked flames and they use much less power than heated emanators, so they can be readily run with batteries for extended periods. This gives them flexibility of placement.

Such devices usually comprise a vibrating plate, a source of power, a reservoir of liquid fragrance and a means to transport the liquid fragrance to the plate for atomisation.

Examples of such devices in the prior art are included in documents JP3342095, US2008041972 A1, US2001042794A, U.S. Pat. Nos. 6,446,880 B1 and 6,341,732 B1. The contents of which are hereby incorporated by reference into the present application.

Problems associated with these devices include obtaining consistent and reliable emanation and leaks. The contact between the piezo vibrating plate and the source of the liquid fragrance must be in finely balanced to allow for successful operation. Drop out and un-atomised spray of the liquids is common when the plates are not vibrating optimally.

SUMMARY OF THE INVENTION

An atomiser for dispensing a fragrance; the atomiser comprising
 a) an outer housing;
 b) an orifice plate and piezo electric element;
 c) a liquid reservoir, comprising a liquid to be atomised, the liquid comprising a fragrance composition and a carrier solvent; and
 d) a liquid transport member
wherein the liquid transport member extends from within the liquid reservoir to abut the orifice plate; and wherein the liquid transport member is substantially contained within the liquid reservoir and both the liquid transport member and liquid reservoir are readily detachable together from the atomiser; and wherein the carrier solvent comprises at least 50% by weight, branched chain alkanes.

DESCRIPTION

Piezo devices and systems for fragrancing the air in the art suffer from a variety of inefficiencies. Poorly aligned interfaces between the vibrating plates and the source of liquid fragrance to be atomised cause many difficulties. As does the rate at which fluid is delivered to the plate from the wick. A low fluid delivery rate means poor fragrance release rate and a high delivery rate gives rise to spray formation (incomplete atomisation).

It has surprisingly been found that a lot of these issues can be resolved by the use of particular solvents as carrier fluids in the fragrancing liquids to be atomised. Liquid fragrance compositions containing high concentrations of branched or iso-alkanes seem to provide excellent atomising properties and delivery properties. Low levels of spray (large particle sizes) and very low residues (particle drop out) are obtained when high levels of branched alkane solvents are used in the carrier liquids.

Fragrance compositions containing at least 50% branched alkanes in the carrier solvent have superior dispensing characteristics in ultrasonic atomising dispensers.

For the purposes of the present invention branched alkanes means any alkanes that are not completely linear. They may have single or multiple branching. Preferred alkanes are iso-alkanes.

Preferably the branched alkanes of the present invention comprise mixtures (or single compounds) with between 11 and 16 carbon atoms.

Commercial examples of useful branched alkanes include the Isopar™ class of products from Exxon mobile. A particularly advantageous branched chain solvent for use in the present invention is Isopar M™.

Preferably the branched alkane carrier solvent has a boiling point of between 240 and 270° C., preferably between 250 and 260 degrees ° C. and most preferably between 252 and 258 degrees ° C.

Preferably the branched alkane carrier solvent has a molecular weight of between 160 and 200, preferably between 185 and 195 and most preferably 188.

Preferably the carrier solvent consists substantially of branched chain alkanes.

The fragrancing liquid of the present invention is preferably composed of a) Fragrance composition 2-25% by weight and b) Carrier solvent 75-98% by weight Preferably the liquid comprises at least 5% by weight of fragrance composition, preferably at least 10% by weight fragrance composition and most preferably at least 15% by weight fragrance composition.

Preferably the liquid comprises at least 50% by weight carrier solvent, preferably at least 75%, more preferably at least 80% and most preferably at least 85% by weight of carrier solvent.

The liquid transport member is a key part of the device. For successful operation the liquid transport member and orifice plate have to interact successfully. The liquid transport member may be made from any suitable material. Preferably the liquid transport member moves liquid from the reservoir to the plate by wicking or capillary action.

Preferably the liquid transport member of the present invention is a wick comprising paper, cotton, nylon, or polypropylene. Most preferably the wick will be formed from polypropylene.

Preferably the wick is between 4 cm and 14 cm in length, more preferably between 5 cm and 12 cm and most preferably between 6 and 10 cm in length.

Preferably the atomiser is powered by battery. Preferably the atomiser comprises at least one battery, and more preferably at least two batteries.

The atomiser may require between 1 and 12 volts to operate, more preferably 3-4.5 volts.

The atomiser may be provided with control circuitry to allow for regular activation of the device over time. Settings may be provided to control length of activation and time between activations. This allows the device to be left in the home or office and provide a constant release of fragrance over many weeks and days.

Activations of the orifice plate to release atomised liquid fragrance composition may last between 1 second and 30 seconds, preferably between 2 seconds and 15 seconds, more preferably between 3 seconds and 10 seconds.

Timing between activations may be between 2 mins and 30 mins, preferably between 5 mins and 20 mins, most preferably between 7 mins and 15 mins.

The skilled person can vary these parameters depending on the intensity of the fragrance desired, strength of fragrance used and concentration of the fragrance composition within the fragrance liquid.

A second aspect to the present invention involves a method of fragrancing the air comprising activating the device of the first aspect of the invention.

This may be manually or automatically by setting up dispensing parameters. Automatic dispensing will require control circuits to activate the device at intervals.

A third aspect of the present invention is a separate refill of fragrance suitable for use as the liquid reservoir with the device of the first aspect of the invention.

This will comprise a container suitable for standalone sale.

Preferably this will be a small flask or bottle. This may be made of any material. Preferably this will be made of glass or plastic.

This will preferably be readily insertable into the atomiser device of the present invention. This should be such that the user may easily remove empty refills. The user may also decide to replace a partially used refill for a refill of a differing fragrance if desired.

The fragrance refill will comprise
1) a liquid; further comprising A fragrance composition and a carrier solvent; and
2) a wick, extending from inside the refill to the outside;
wherein the carrier solvent comprises at least 50% by weight of branched alkanes.

Including the wick with the refills prevents the mixing of fragrances in the wick. A rapid fragrance change can be carried out without blending different fragrances.

Wicks can get clogged in time. Using a new wick with each refill prevents this from happening.

The refill may comprises at least 5% by weight of fragrance composition, preferably at least 10% by weight fragrance composition and most preferably at least 15% by weight fragrance composition.

The refill liquid may comprise at least 60% by weight carrier solvent, preferably at least 75%, more preferably at least 80% and most preferably at least 85% by weight of carrier solvent.

The carrier solvent may comprises at least 60% by weight of branched alkanes, preferably at least 70% by weight of branched alkanes and most preferably at least 90% by weight branched alkanes.

The carrier solvent of the refill may consist entirely of branched-alkanes.

The branched alkane carrier solvent may have a boiling point of between 240 and 270° C., preferably between 250 and 260° C. and most preferably between 252 and 258 degrees ° C.

The branched alkane carrier solvent may have a molecular weight of between 170 and 200, preferably between 185 and 195 and most preferably 188.

A particularly preferred refill contains:
15% by weight of fragrance composition; and
85% by weight of a branched alkane solvent.

More preferably the branched alkane solvent comprises Isopar-M®.

A device comprising the refill above and a polypropylene wick has been shown to yield excellent fragrance dispersion characteristics with virtually no residues remaining.

The invention claimed is:

1. An atomiser adapted to dispense a fragrancing liquid comprising a fragrance composition; the atomiser comprising
an outer housing;
an orifice plate and piezo electric element;
a liquid reservoir, comprising the fragrancing liquid to be atomised, the fragrancing liquid comprising the fragrance composition and a carrier solvent; and,
a liquid transport member;
wherein the liquid transport member extends from within the liquid reservoir to abut the orifice plate; and
wherein the liquid transport member is a wick comprising paper, cotton, nylon, or polypropylene which is substantially contained within the liquid reservoir and both the wick and liquid reservoir are readily detachable together from the atomiser; and
wherein the fragrancing liquid comprises 2-25% wt. of the fragrance composition, and,
75-98% wt. of the carrier solvent which comprises at least 50% wt. branched chain alkanes.

2. The atomiser of claim 1 wherein wick comprises polypropylene.

3. The atomiser claim 1, wherein the fragrancing liquid comprises at least 5% by weight of the fragrance composition.

4. The atomiser of claim 1, wherein the carrier solvent is greater than 99% by weight the branched alkane solvent.

5. The atomiser of claim 1, wherein the branched chain alkane carrier solvent comprises $C_{11}$-$C_{16}$ carbon compounds.

6. The atomiser of claim 1, wherein the branched chain alkane carrier solvent has a boiling point of between 240 and 270° C.

7. The atomiser of claim 1, wherein the branched chain alkane carrier solvent has a molecular weight of between 170 and 200.

8. The atomiser of claim 1, wherein the carrier solvent consists of the branched chain alkanes.

9. The atomiser of claim 1, wherein the atomiser comprises at least one battery.

10. The atomiser of claim 1, wherein the atomiser requires between 1 and 12 volts to operate.

11. The atomiser of claim 1, which additionally comprises control circuitry operative to provide regular activation of the device over time.

12. A method of fragrancing the air comprising activating the atomizer of claim 1.

13. A refill for the atomizer of claim 1 adapted for use as the liquid reservoir comprising;
the fragrancing liquid comprising the
fragrance composition and the carrier solvent; and
the wick, extending from inside the refill to the outside.

14. The refill of claim 13 wherein the fragrancing liquid comprises at least 5% by weight of fragrance composition.

15. The refill of claim 13, wherein the carrier solvent is comprises at least 60% by weight of branched chain alkanes.

16. The refill of claim 13, wherein the carrier solvent consists of the branched chain alkanes.

17. The refill of claim 13, wherein the branched alkanes comprise $C_{11}$ to $C_{16}$ branched chain alkanes.

18. The refill of claim 13, wherein the branched chain alkane carrier solvent has a boiling point of between 240 and 270° C.

19. The refill of claim 13, wherein the branched chain alkane carrier solvent has a molecular weight of between 170 and 200.

20. The atomizer of claim 1 wherein the wick is between 4 cm and 14 cm in length.

* * * * *